(12) United States Patent
Matsuzaki

(10) Patent No.: US 9,051,276 B2
(45) Date of Patent: Jun. 9, 2015

(54) COMPOSITION FOR CONTROLLING PLANT DISEASES AND USE THEREOF

(71) Applicant: SUMITOMO CHEMICAL COMPANY, LIMITED, Tokyo (JP)

(72) Inventor: Yuichi Matsuzaki, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 14/370,939

(22) PCT Filed: Jan. 8, 2013

(86) PCT No.: PCT/JP2013/050078
§ 371 (c)(1),
(2) Date: Jul. 7, 2014

(87) PCT Pub. No.: WO2013/105543
PCT Pub. Date: Jul. 18, 2013

(65) Prior Publication Data
US 2015/0005495 A1 Jan. 1, 2015

(30) Foreign Application Priority Data
Jan. 10, 2012 (JP) .................................. 2012-001918

(51) Int. Cl.
| | |
|---|---|
| *A61K 31/33* | (2006.01) |
| *C07D 237/00* | (2006.01) |
| *C07D 237/24* | (2006.01) |
| *A01N 43/58* | (2006.01) |
| *A01N 43/56* | (2006.01) |
| *C07D 237/08* | (2006.01) |
| *C07D 237/12* | (2006.01) |

(52) U.S. Cl.
CPC .............. *C07D 237/24* (2013.01); *A01N 43/58* (2013.01); *A01N 43/56* (2013.01); *C07D 237/08* (2013.01); *C07D 237/12* (2013.01)

(58) Field of Classification Search
USPC .......................................... 514/183; 544/224
See application file for complete search history.

(56) References Cited

U.S. PATENT DOCUMENTS

| | | |
|---|---|---|
| 2008/0194566 A1 | 8/2008 | Morishita et al. |
| 2008/0275050 A1 | 11/2008 | Morishita et al. |
| 2010/0130359 A1 | 5/2010 | Dietz et al. |
| 2013/0131067 A1 | 5/2013 | Matsuzaki |
| 2013/0137658 A1 | 5/2013 | Matsuzaki |
| 2013/0137683 A1 | 5/2013 | Matsuzaki |
| 2013/0137692 A1 | 5/2013 | Matsuzaki |

FOREIGN PATENT DOCUMENTS

| | | |
|---|---|---|
| EP | 2 014 167 A1 | 1/2009 |
| WO | WO 2005/121104 A1 | 12/2005 |
| WO | WO 2005/121107 A1 | 12/2005 |
| WO | WO 2006/001175 A1 | 1/2006 |
| WO | WO 2008/135413 A1 | 11/2008 |
| WO | WO 2009/118297 A2 | 10/2009 |
| WO | WO 2010/047866 A2 | 4/2010 |
| WO | WO 2011/028996 A2 | 3/2011 |
| WO | WO 2012/020772 A1 | 2/2012 |
| WO | WO 2012/020774 A1 | 2/2012 |
| WO | WO 2012/020776 A1 | 2/2012 |
| WO | WO 2012/020778 A1 | 2/2012 |

OTHER PUBLICATIONS

Tomlin et al., "The Pesticide Manual," 14th Edition, 2006, 19 pages.
International Search Report (form PCT/ISA/210), dated Mar. 19, 2013, for International Application No. PCT/JP2013/050078.
International Search Report (form PCT/ISA/210), dated Mar. 19, 2013, for International Application No. PCT/JP2013/050079.
International Search Report (form PCT/ISA/210), dated Mar. 19, 2013, for International Application No. PCT/JP2013/050080.
International Search Report (form PCT/ISA/210), dated Mar. 5, 2013, for International Application No. PCT/JP2013/050075.
International Search Report (form PCT/ISA/210), dated Mar. 5, 2013, for International Application No. PCT/JP2013/050076.
International Search Report (form PCT/ISA/210), dated Mar. 5, 2013, for International Application No. PCT/JP2013/050077.

*Primary Examiner* — Jeffrey H Murray
*Assistant Examiner* — Oluwafemi Masha
(74) *Attorney, Agent, or Firm* — Birch, Stewart, Kolasch & Birch, LLP

(57) ABSTRACT

A composition for controlling plant diseases, containing a pyridazine compound represented by Formula (I) and fipronil, exhibits an excellent control effect against plant diseases. The present invention provides a composition for controlling plant diseases, containing the pyridazine compound represented by Formula (I) and fipronil, and a method for controlling plant diseases, including a step of applying an effective amount of the pyridazine compound represented by Formula (I) and fipronil to a plant or soil for cultivating a plant.

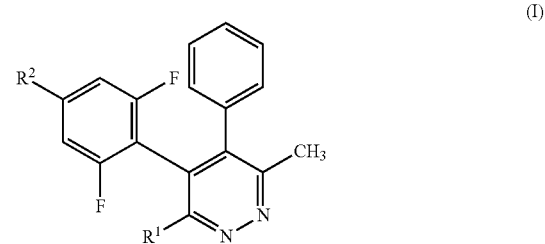

(I)

[In the formula, $R^1$ represents a chlorine atom, a bromine atom, a cyano group, or a methyl group, and $R^2$ represents a hydrogen atom or a fluorine atom.]

6 Claims, No Drawings

COMPOSITION FOR CONTROLLING PLANT DISEASES AND USE THEREOF

TECHNICAL FIELD

The present invention relates to a composition for controlling plant diseases and a use thereof.

BACKGROUND ART

In the related art, many compounds have been developed for controlling plant diseases, and put into practical use (for example, refer to PTLs 1 and 2).

BACKGROUND DOCUMENT

Patent Document

[Patent Document 1] Pamphlet of International Publication No. 2005/121104
[Patent Document 2] Pamphlet of International Publication No. 2006/001175

SUMMARY OF THE INVENTION

Problems to be Solved by the Invention

An object of the present invention is to provide a composition having an excellent control effect against plant diseases.

Means for Solving Problems

The present inventor has studied to find a composition having an excellent controlling effect against plant diseases, and as a result, has found that a composition for controlling plant diseases containing a pyridazine compound represented by the following Formula (I) and fipronil has an excellent control effect against plant diseases, and completed the present invention.

That is, the invention is as follows.

[1] A composition for controlling plant diseases, containing a pyridazine compound represented by Formula (I) and fipronil.

Formula (I)

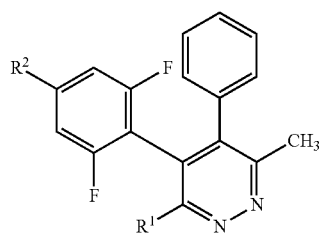

(I)

[In the formula, $R^1$ represents a chlorine atom, a bromine atom, a cyano group, or a methyl group, and $R^2$ represents a hydrogen atom or a fluorine atom.]

[2] The composition for controlling plant diseases according to [1], in which the weight ratio of the pyridazine compound to fipronil (the pyridazine compound/fipronil) is 1/1 to 1/100.

[3] A method for controlling plant diseases, including a step of applying an effective amount of a pyridazine compound represented by Formula (I) and fipronil to a plant or soil for cultivating a plant.

Formula (I)

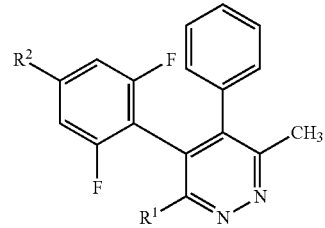

(I)

[In the formula, $R^1$ represents a chlorine atom, a bromine atom, a cyano group, or a methyl group, and $R^2$ represents a hydrogen atom or a fluorine atom.]

[4] The method for controlling plant diseases according to [3], in which a weight ratio of the pyridazine compound to fipronil (the pyridazine compound/fipronil) is 1/1 to 1/100.

[5] The method for controlling plant diseases according to [3] or [4], in which a plant or soil for cultivating a plant is wheat or soil for cultivating wheat.

[6] The method for controlling plant diseases according to [3] or [4], in which a plant or soil for cultivating a plant is plant seeds.

[7] Plant seeds, in which a pyridazine compound represented by Formula (I) and fipronil are penetrated into the inside thereof or attached to a surface thereof.

Formula (I)

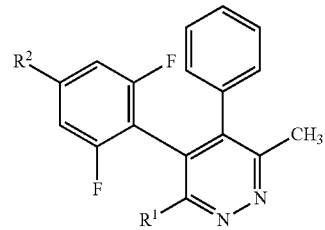

(I)

[In the formula, $R^1$ represents a chlorine atom, a bromine atom, a cyano group, or a methyl group, and $R^2$ represents a hydrogen atom or a fluorine atom.]

Effects of the Invention

According to the invention, it is possible to control plant diseases.

MODE FOR CARRYING OUT THE INVENTION

A composition for controlling plant diseases of the present invention (hereinafter, described as "the composition of the present invention") contains a pyridazine compound represented by Formula (I) (hereinafter, described as "the pyridazine compound") and fipronil.

Formula (I)

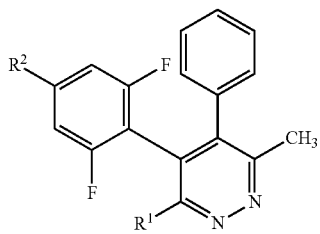

(I)

[In the formula, $R^1$ represents a chlorine atom, a bromine atom, a cyano group, or a methyl group, and $R^2$ represents a hydrogen atom or a fluorine atom.]

As an aspect of the pyridazine compound used in the composition of the present invention, for example, the following pyridazine compounds can be exemplified.

A pyridazine compound in which $R^1$ is a chlorine atom or a methyl group, in Formula (I);

a pyridazine compound in which $R^1$ is a chlorine atom, in Formula (I);

a pyridazine compound in which $R^1$ is a methyl group, in Formula (I);

a pyridazine compound in which $R^1$ is a cyano group, in Formula (I);

a pyridazine compound in which $R^2$ is a hydrogen atom, in Formula (I);

a pyridazine compound in which $R^2$ is a fluorine atom, in Formula (I);

a pyridazine compound in which $R^1$ is a chlorine atom, a cyano group, or a methyl group, and $R^2$ is a hydrogen atom, in Formula (I); and a pyridazine compound in which $R^1$ is a chlorine atom, a cyano group, or a methyl group, and $R^2$ is a fluorine atom, in Formula (I).

Specifically, examples of the pyridazine compound include the following.

A pyridazine compound in which $R^1$ is a chlorine atom, and $R^2$ is a hydrogen atom, in Formula (I) (hereinafter, described as "the pyridazine compound (1)");

a pyridazine compound in which $R^1$ is a bromine atom, and $R^2$ is hydrogen atom, in Formula (I) (hereinafter, described as "the pyridazine compound (2)");

a pyridazine compound in which $R^1$ is a cyano group, and $R^2$ is a hydrogen atom, in Formula (I) (hereinafter, described as "the pyridazine compound (3)");

a pyridazine compound in which $R^1$ is a methyl atom, and $R^2$ is a hydrogen atom, in Formula (I) (hereinafter, described as "the pyridazine compound (4)");

a pyridazine compound in which $R^1$ is a chlorine atom, and $R^2$ is a fluorine atom, in Formula (I) (hereinafter, described as "the pyridazine compound (5)");

a pyridazine compound in which $R^1$ is a bromine atom, and $R^2$ is a fluorine atom, in Formula (I) (hereinafter, described as "the pyridazine compound (6)");

a pyridazine compound in which $R^1$ is a cyano group, and $R^2$ is a fluorine atom, in Formula (I) (hereinafter, described as "the pyridazine compound (7)"); and a pyridazine compound in which $R^1$ is a methyl atom, and $R^2$ is a fluorine atom, in Formula (I) (hereinafter, described as "the pyridazine compound (8)").

A pyridazine compound in which $R^1$ is a chlorine atom or a bromine atom in Formula (I) among the pyridazine compounds can be prepared by a method disclosed in Pamphlet of international Publication No 2005/121104.

A pyridazine compound in which $R^1$ is a methyl group in Formula (I) among the pyridazine compounds can be prepared by a method disclosed in Pamphlet of International Publication No. 2006/001175.

A compound (I-2) in which $R^1$ is a cyano group in Formula (I) among the pyridazine compounds can be prepared by reacting a compound (I-1) in which $R^1$ is a bromine atom in Formula (I) among the pyridazine compounds with copper cyanide.

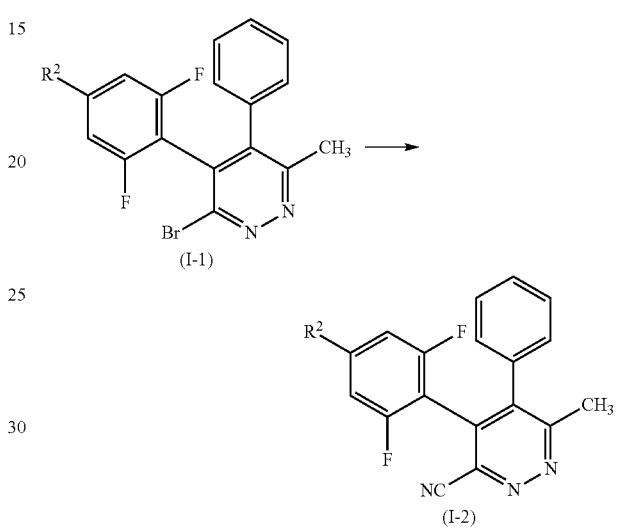

[In the formula, $R^2$ represents the same definition as described above.]

This reaction is usually performed in the presence of a solvent.

Examples of the solvent used in the reaction include aprotic polar solvents such as N,N-dimethylacetamide, and the like.

An amount of the copper cyanide used in the reaction is usually a ratio of 1 mole to 1.5 moles with respect to 1 mole of the compound (I-1).

The reaction temperature of the reaction is usually in a range of 120° C. to 180° C., and the reaction time is usually in a range of 1 hour to 24 hours.

After the reaction is completed, for example, an operation in which the reaction mixture is mixed with water and an organic solvent, filtration is performed, the filtrate is separated, and the obtained organic layer is further washed with water, dried, and concentrated is performed, whereby the compound (I-2) can be isolated. The isolated compound (I-2) can also be further purified by chromatography, recrystallization, and the like.

A compound (I-4) in which $R^1$ is a methyl group in Formula (I) among the pyridazine compounds can be prepared by reacting a compound (I-3) in which $R^1$ is a chlorine atom among the pyridazine compounds with a Grignard reagent represented by Formula (2) in the presence of an iron catalyst.

$$CH_3-MgX \quad (2)$$

[In the formula, X represents a bromine atom or a chlorine atom.]

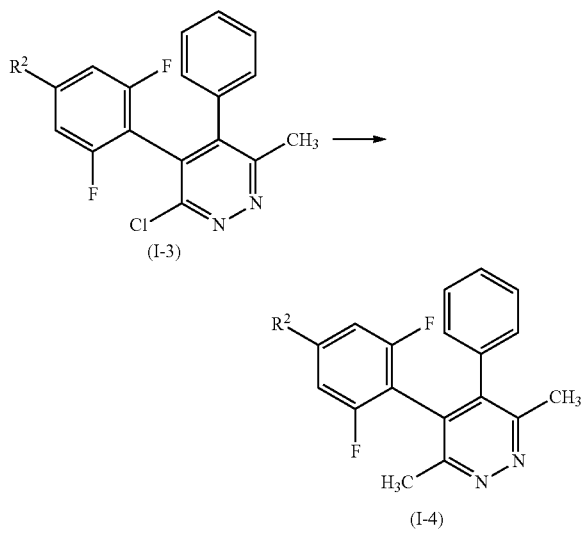

[In the formula, $R^2$ represents the same definition as described above.]

This reaction is usually performed in the presence of a solvent.

Examples of the solvent used in the reaction include tetrahydrofuran, diethyl ether, N-methylpyrrolidone, and a mixed solvent thereof. In a case where the reaction solvent is a mixture of tetrahydrofuran and N-methylpyrrolidone, a mixing ratio between tetrahydrofuran and N-methylpyrrolidone is usually in a range of 30:1 to 3:1 by volume ratio.

Examples of the iron catalyst used in the reaction include iron (III) acetylacetonate, iron (III) chloride, and the like. An amount of the iron catalyst used in the reaction is usually a ratio of 0.01 moles to 0.3 moles with respect to 1 mole of the compound (I-3).

The reaction temperature of the reaction is usually in a range of −20° C. to 30° C., and the reaction time is usually in a range of 0.1 hours to 6 hours.

After the reaction completed, for example, an operation in which the reaction mixture is mixed with hydrochloric acid, extraction is performed using an organic solvent, and the obtained organic layer is washed with water, dried, and concentrated, whereby the compound (I-4) can be isolated. The isolated compound (I-4) can also be further purified by chromatography, recrystallization, and the like.

Fipronil is a known compound, and for example, there are described in "THE PESTICIDE MANUAL-14th EDITION (published by BCPC), ISBN 1901396142". Fipronil can be obtained from commercially available formulations or synthesized by known methods.

A weight ratio between the pyridazine compound and fipronil (the pyridazine compound/fipronil) in the composition of the present invention is usually 1/500 to 500/1 and preferably 1/1 to 1/100.

The composition of the present invention may be a mixture of the pyridazine compound and fipronil itself, and in general, the composition of the present invention is formulated into oil, emulsion, a flowable agent, a wettable powder, a granulated wettable powder, a powder agent, and granules by mixing the pyridazine compound, fipronil, and an inactive carrier, and adding a surfactant or other adjuvants for formulation if necessary. The formulation can be used as a formulation for controlling plant diseases, without any changes or by adding other inactive ingredients.

In the composition of the present invention, the pyridazine compound and fipronil are usually contained by 0.1% by weight to 99% by weight, preferably 0.2% by weight to 90% by weight, and more preferably 1% by weight to 80% by weight in total.

Examples of the solid carriers used for formulation include fine powdery or granular materials and the like formed of minerals such as kaolin clay, attapulgite clay, bentonite, montmorillonite, Japanese acid clay, pyrophyllite, talc, diatomaceous earth, and calcite, natural organic substances such as corn rachis powder and walnut shell powder, synthetic organic substances such as urea, salts such as calcium carbonate and ammonium sulfate, or synthetic inorganic substances such as synthetic hydrated silicon oxide. Examples of the liquid carriers include aromatic hydrocarbons such as xylene, alkylbenzene, and methylnaphthalene, alcohols such as 2-propanol, ethylene glycol, propylene glycol, and ethylene glycol monoethyl ether, ketones such as acetone, cyclohexanone, and isophorone, plant oil such as soybean oil and cotton seed oil, petroleum-based aliphatic hydrocarbons, esters, dimethylsulfoxide, acetonitrile, water, and the like.

Examples of the surfactants include anionic surfactants such as an alkyl sulfuric acid ester salt, an alkyl aryl sulfonic acid salt, a dialkyl sulfosuccinic acid salt, a polyoxyethylene alkyl aryl ether phosphoric acid ester salt, a lignin sulfonic acid salt, and a naphthalene sulfonate formaldehyde polycondensate, nonionic surfactants such as a polyoxyethylene alkyl aryl ether, a polyoxyethylene alkyl polyoxypropylene block copolymer, and a sorbitan fatty acid ester, and cationic surfactants such as an alkyl trimethyl ammonium salt.

Examples of other adjuvants for formulation include water-soluble polymers such as polyvinyl alcohol and polyvinyl pyrrolidone, gum Arabic, alginic acid and a salt thereof, polysaccharides such as CMC (carboxymethylcellulose) and xanthan gum, inorganic substances such as aluminum magnesium silicate and alumina sol, preservatives, colorants, and stabilizing agents such as PAP (isopropyl acid phosphate) and BHT.

In addition, when the pyridazine compound and fipronil are formulated by each method described above, after diluting with water if necessary, the composition of the present invention is prepared by mixing each formulation or the diluted solution thereof.

The composition of the present invention is used to protect plants from plant diseases.

Examples of the plant diseases on which the composition of the present invention has controlling effects include the following.

Rice diseases: blast (*Magnaporthe grisea*), brown spot (*Cochliobolus miyabeanus*), sheath blight (*Rhizoctonia solani*), and bakanae (*Gibberella fujikuroi*).

Wheat diseases: powdery mildew (*Erysiphe graminis*), Fusarium head blight (*Fusarium graminearum, F. avenacerum, F. culmorum, Microdochium nivale*), rust (*Puccinia striiformis, P. graminis, P. recondita*), pink snow rot (*Microdochium nivale*), Typhula snow blight (*Typhula sp.*), loose smut (*Ustilago tritici*), smut (*Tilletia caries*), Eyespot (*Pseudocercosporella herpotrichoides*), leaf blight (*Mycosphaerell graminicola*), septoria leaf spot (*Stagonospora nodorum*), and tan spot (*Pyrenophora tritici-repentis*).

Barley diseases: powdery mildew (*Erysiphe graminis*), Fusarium head blight (*Fusarium graminearum, F. avenacerum, F. culmorum, Microdochium nivale*), rust (*Puccinia striiformis, P. graminis, P. hordei*), loose smut (*Ustilago tritici*), leaf blotch (*Rhynchosporium secalis*), net blotch (*Pyrenophora teres*), leaf spot (*Cochliobolus sativus*), stripe (*Pyrenophora graminea*), and *Rhizoctonia* damping-off (*Rhizoctonia solani*).

Corn diseases: smut (*Ustilago maydis*), brown leaf spot (*Cochliobolus heterostrophus*), copper spot (*Gloeocercospora sorghi*), southern rust (*Puccinia polysora*), gray leaf spot (*Cercospora zeae-maydis*), and *Rhizoctonia* damping-off (*Rhizoctonia solani*).

Citrus diseases: melanose (*Diaporthe citri*), scab (*Elsinoe fawcetti*), green mold (*Penicillium digitatum*) and blue mold (*Penicillium italicum*), and brown rot (*Phytophthora parasitica, Phytophthora citrophthora*).

Apple diseases: blossom blight (*Monilinia mali*), canker (*Valsa ceratosperma*), powdery mildew (*Podosphaera leucotricha*), *Alternaria* leaf spot (*Alternaria alternata* apple pathotype), scab (*Venturia inaequalis*), bitter rot (*Colletotrichum acutatum*), and crawn rot (*Phytophthora cactorum*).

Pear Diseases: scab (*Venturia nashicola, V. pirina*), black spot (*Alternaria alternata* Japanese pear pathotype), rust (*Gymnosporangium haraeanum*), phytophthora fruit rot (*Phytophthora cactorum*).

Peach diseases: brown rot (*Monilinia fructicola*), scab (*Cladosporium carpophilum*) and *Phomopsis* rot (*Phomopsis* sp.).

Grapes diseases: anthracnose (*Elsinoe ampelina*), ripe rot (*Glomerella cingulata*), powdery mildew (*Uncinula necator*), rust (*Phakopsora ampelopsidis*), black rot (*Guignardia bidwellii*), and downy mildew (*Plasmopara viticola*).

Japanese persimmon diseases: anthracnose (*Gloeosporium kaki*) and leaf spot (*Cercospora kaki, Mycosphaerella nawae*).

Gourd family diseases: anthracnose (*Colletotrichum lagenarium*), powdery mildew (*Sphaerotheca fuliginea*), gummy stem blight (*Mycosphaerella melonis*), *Fusarium* wilt (*Fusarium oxysporum*), downy mildew (*Pseudoperonospora cubensis*), *Phytophthora* rot (*Phytophthora* sp.), and damping-off (*Pythium* sp.).

Tomato diseases: early blight (*Alternaria solani*), leaf mold (*Cladosporium flavum*), and late blight (*Phytophthora infestans*).

Egg plant diseases: brown spot (*Phomopsis vexans*) and powdery mildew (*Erysiphe cichoracearum*).

Cruciferous vegetable diseases: *Alternaria* leaf spot (*Alternaria japonica*), white spot (*Cercosporella brassicae*), clubroot (*Plasmodiophora brassicae*), and downy mildew (*Peronospora parasitica*).

Welsh onion diseases: rust (*Puccinia allii*) and downy mildew (*Peronospora destructor*).

Soybean diseases: purple seed stain (*Cercospora kikuchii*), sphaceloma scad (*Elsinoe glycines*), pod and stem blight (*Diaporthe phaseolorum* var. *sojae*), septoria brown spot (*Septoria glycines*), frogeye leaf spot (*Cercospora sojina*), rust (*Phakopsora pachyrhizi*), brown stem rot (*Phytophthora sojae*), *Rhizoctonia* damping-off (*Rhizoctonia solani*), target spot (*Corynespora casiicola*), and sclerotinia rot (*Sclerotinia sclerotiorum*).

Kidney bean disease: anthracnose (*Colletotrichum lindemthianum*).

Peanut diseases: leaf spot (*Cercospora personata*), brown leaf spot (*Cercospora arachidicola*), and southern blight (*Sclerotium rolfsii*);

Garden pea disease: powdery mildew (*Erysiphe pisi*).

Potato diseases: early blight (*Alternaria solani*), late blight (*Phytophthora infestans*), pink rot (*Phytophthora erythroseptica*), and powdery scab (*Spongospora subterranean*, f. sp. *subterranea*).

Strawberry diseases: powdery mildew (*Sphaerotheca humuli*) and anthracnose (*Glomerella cingulata*).

Tea diseases: net blister blight (*Exobasidium reticulatum*), white scab (*Elsinoe leucospila*), gray blight (*Pestalotiopsis* sp.), and anthracnose (*Colletotrichum theae-sinensis*).

Tobacco diseases: brown spot (*Alternaria longipes*), powdery mildew (*Erysiphe cichoracearum*), anthracnose (*Colletotrichum tabacum*), downy mildew (*Peronospora tabacina*), and black shank (*Phytophthora nicotianae*).

Rapeseed diseases: sclerotinia rot (*Sclerotinia sclerotiorum*) and *Rhizoctonia* damping-off (*Rhizoctonia solani*).

Cotton disease: *Rhizoctonia* damping-off (*Rhizoctonia solani*).

Sugar beet diseases: *Cercospora* leaf spot (*Cercospora beticola*), leaf blight (*Thanatephorus cucumeris*), root rot (*Thanatephorus cucumeris*), and *Aphanomyces* root rot (*Aphanomyces cochlioides*).

Rose diseases: black spot (*Diplocarpon rosae*), powdery mildew (*Sphaerotheca pannosa*), and downy mildew (*Peronospora sparsa*).

Diseases of *chrysanthemum* and *asteraceous* vegetables: downy mildew (*Bremia lactucae*), leaf blight (*Septoria chrysanthemi-indici*), and white rust (*Puccinia horiana*).

Diseases of various crops: diseases caused by *Pythium* spp. (*Pythium aphanidermatum, Pythium debarianum, Pythium graminicola, Pythium irregulare, Pythium ultimum*), gray mold (*Botrytis cinerea*), and *Scierotinia* rot (*Sclerotinia sclerotiorum*).

Radish disease: *Alternaria* leaf spot (*Alternaria brassicicola*).

Turfgrass diseases: dollar spot (*Scierotinia homeocarpa*), and brown patch and large patch (*Rhizoctonia solani*).

Banana disease: sigatoka (*Mycosphaerella fijiensis, Mycosphaerella musicola*).

Sunflower disease: downy mildew (*Plasmopara halstedii*).

Seed diseases or diseases in the early stages of the growth of various plants caused by bacteria of *Aspergillus* spp., *Penicillium* spp., *Fusarium* spp., *Gibberella* spp., *Tricoderma* spp., *Thielaviopsis* spp., *Rhizopus* spp., *Mucor* spp., *Corticium* spp., *Phoma* spp., *Rhizoctonia* spp. and *Diplodia* spp.

Viral diseases of various plants mediated by *Polymixa* genus or *Olpidium* genus.

Examples of plants to which the composition of the present invention is applicable include the following.

Crops: corn, rice, wheat, barley, rye, oat, sorghum, cotton, soybean, peanut, buckwheat, sugar beet, rapeseed, sunflower, sugar cane, tobacco and the like, Vegetables: solanaceous vegetables (eggplant, tomato, pimento, pepper, potato, or the like), cucurbitaceous vegetables (cucumber, pumpkin, zucchini, watermelon, melon, squash, or the like), cruciferous vegetables (Japanese radish, turnip, horseradish, kohlrabi, Chinese cabbage, cabbage, leaf mustard, broccoli, cauliflower, or the like), asteraceous vegetables (burdock, crown daisy, artichoke, lettuce, or the like) liliaceous vegetables (green onion, onion, garlic, and asparagus), ammiaceous vegetables (carrot, parsley, celery, parsnip, or the like), chenopodiaceous vegetables (spinach, Swiss chard, or the like), lamiaceous vegetables (*Perilla frutescens*, mint, basil, or the like), strawberry, sweet potato, *Dioscorea japonica*, colocasia, or the like, Flowers, Foliage plants, Turf grasses, Fruits: pomaceous fruits (apple, pear, Japanese pear, Chinese quince, quince, or the like), stone fleshy fruits (peach, plum, nectarine, *Prunus mume*, cherry fruit, apricot, prune, or the like), citrus fruits (Citrus unshiu, orange, lemon, lime, grapefruit, or the like), nuts (chestnuts, walnuts, hazelnuts, almond, pistachio, cashew nuts, macadamia nuts, or the like), berries (blueberry, cranberry, blackberry, raspberry, or the like), grape, Japanese persimmon, olive, Japanese plum, banana, coffee, date palm, coconuts, or the like, Trees other than fruit trees; tea, mulberry, flowering plant, roadside trees (ash, birch, dogwood, Eucalyptus, *Ginkgo biloba*, lilac, maple, Quercus, poplar, *Cercis chinensis*, *Liquidambar formosana*, plane tree, zelkova, Japanese arborvitae, fir wood, hemlock, juniper, *Pinus, Picea*, and *Taxus cuspidate*), or the like.

The plants described above may be plants to which resistance is applied by gene recombination techniques.

Among the above, in particular, high control effect against plant diseases that occur in wheat is expected.

In addition, among plant diseases that occur in these crops, examples of diseases of wheat to which particularly high control effect is expected include powdery mildew (*Erysiphe graminis*), *fusarium* head blight (*Fusarium graminearum, F. avenacerum, F. culmorum, Microdochium nivale*), rust (*Puccinia striiformis, P. graminis, P. recondita*), snow mold (*Microdochium nivale*), *Typhula* snow blight (*Typhula* spp.), loose smut (*Ustilago tritici*), smut (*Tilletia caries*), Eyespot (*Pseudocercosporella herpotrichoides*), leaf blight (*Mycosphaerella graminicola*), *septoria* leaf spot (*Stagonospora nodorum*), and tan spot (*Pyrenophora tritici-repentis*).

An aspect of the composition of the present invention includes the following.

A composition containing the pyridazine compound (1) and fipronil;

a composition containing the pyridazine compound (2) and fipronil;

a composition containing the pyridazine compound (3) and fipronil;

a composition containing the pyridazine compound (4) and fipronil;

a composition containing the pyridazine compound (5) and fipronil;

a composition containing the pyridazine compound (6) and fipronil;

a composition containing the pyridazine compound (7) and fipronil;

a composition containing the pyridazine compound (8) and fipronil;

a composition containing the pyridazine compound (1) and fipronil by weight ratio (the pyridazine compound (1)/fipronil) of 1/1 to 1/100;

a composition containing the pyridazine compound (2) and fipronil by weight ratio (the pyridazine compound (2)/fipronil) of 1/1 to 1/100;

a composition containing the pyridazine compound (3) and fipronil by weight ratio (the pyridazine compound (3)/fipronil) of 1/1 to 1/100;

a composition containing the pyridazine compound (4) and fipronil by weight ratio (the pyridazine compound (4)/fipronil) of 1/1 to 1/100;

a composition containing the pyridazine compound (5) and fipronil by weight ratio (the pyridazine compound (5)/fipronil) of 1/1 to 1/100;

a composition containing the pyridazine compound (6) and fipronil by weight ratio (the pyridazine compound (6)/fipronil) of 1/1 to 1/100;

a composition containing the pyridazine compound (7) and fipronil by weight ratio (the pyridazine compound (7)/fipronil) of 1/1 to 1/100; and a composition containing the pyridazine compound (8) and fipronil by weight ratio (the pyridazine compound (8)/fipronil) of 1/1 to 1/100.

As the method for controlling plant diseases of the present invention (hereinafter, described as the control method of the present invention), a method in which an effective amount of the pyridazine compound and fipronil is applied to a plant or soil for cultivating a plant can be exemplified. As the plant, for example, foliage of a plant, seeds of a plant, and bulbs of a plant can be exemplified. Moreover, the bulbs mean discoid stems, corms, rhizomes, tubers, tuberous roots, and rhizophores.

In the control method of the present invention, the pyridazine compound and fipronil may be separately applied to a plant or soil for cultivating a plant in the same period. The pyridazine compound and fipronil are usually applied as the composition of the present invention from the viewpoint of simplicity during the treatment.

In the control method of the present invention, examples of the method of treating the pyridazine compound and fipronil include a foliar treatment, a soil treatment, a root treatment, and a seed treatment.

Examples of the foliar treatment include a method of treating the pyridazine compound and fipronil onto surface of a plant which is cultivated, by spraying to foliage or a trunk.

Examples of the root treatment include a method of immersing a whole plant or a root part of a plant into a drug solution containing the pyridazine compound and fipronil and a method of attaching a solid formulation containing the pyridazine compound, fipronil, and a solid carrier to roots of a plant.

Examples of the soil treatment include spraying onto the soil, admixing with the soil, and perfusion of a drug solution into the soil.

Examples of the seed treatment include a treatment of seeds or bulbs of a plant to be protected from plant diseases with the composition of the present invention, and specifically, examples thereof include a spraying treatment in which a suspension of the composition of the present invention is sprayed onto a seed surface or a bulb surface in the form of mist, a smearing treatment in which wettable powder, an emulsion, or a flowable agent of the composition of the present invention is used as it is or used by being added with a small amount of water so as to coat seeds or bulbs, a immersing treatment in which seeds are immersed in the solution of the composition of the present invention for a certain period of time, a film coating treatment, a pellet coating treatment, and the like.

In the control method of the present invention, the amount for the treatment of the pyridazine compound and fipronil may be changed depending on the kind of the plant to be treated, the kind and the frequency of occurrence of the plant diseases to be controlled, a formulation form, a treatment period, a treatment method, a treatment place, a climatic condition and the like, and in a case where the pyridazine compound and fipronil are applied to foliage of a plant, or in a case where the pyridazine compound and fipronil are applied to soil for cultivating a plant, the total amount of the pyridazine compound and fipronil per 1000 $m^2$ is usually 1 g to 500 g, preferably 2 g to 200 g, and more preferably 10 g to 100 g. In addition, the amount for the treatment of the pyridazine compound and fipronil per 1 kg of seeds in the seed treatment is usually 0.001 g to 10 g, and preferably 0.01 g to 1 g as the total amount of the pyridazine compound and fipronil.

An emulsion, wettable powder, a flowable agent, or the like is usually diluted with water, and then sprayed for treatment. In this case, the concentration of the pyridazine compound and fipronil is usually in the range of 0.0005% by weight to 2% by weight and preferably 0.005% by weight to 1% by weight as the total concentration of the pyridazine compound and fipronil. A powder agent, a granule agent or the like is usually used for treatment without being diluted.

In the present invention, seeds of a plant to which an effective amount of the pyridazine compound and fipronil are applied are seeds into which the pyridazine compound and fipronil are penetrated or seeds with the surface to which the pyridazine compound and fipronil are attached. The amount of the pyridazine compound and fipronil which is penetrated or attached in the seeds is usually 0.001 g to 10 g and preferably 0.01 g to 1 g as the total amount per 1 kg of seeds. The weight ratio between the pyridazine compound and fipronil in the seeds (the pyridazine compound/fipronil) is usually 1/500 to 500/1 and preferably 1/1 to 1/100.

EXAMPLES

Hereinafter, formulation examples and test examples of the present invention will be described in more detail, and the present invention is not limited to the following examples. Moreover, in the following examples, "part(s)" represents "part(s) by weight" unless otherwise specified.

First, reference preparation examples of the pyridazine compound used in the composition of the present invention will be described in more detail, and the present invention is not limited to these examples.

Reference Preparation Example 1

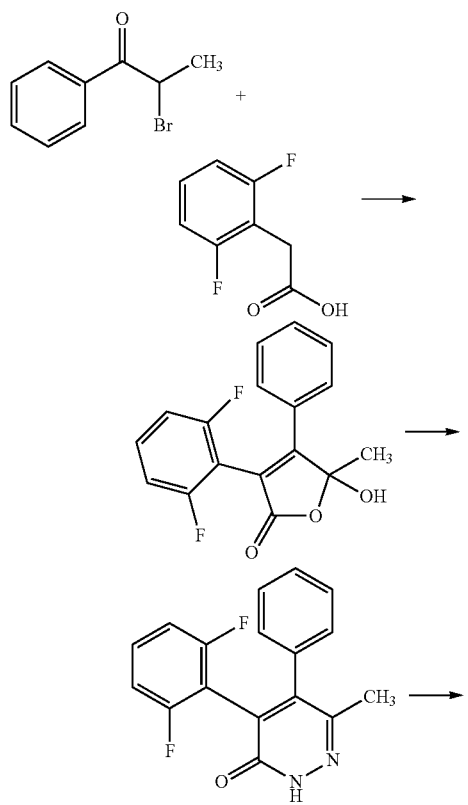

1.52 g of triethylamine was added dropwise to a mixture of 2.13 g of 2-bromopropiophenone, 1.81 g of 2,6-difluorophenyl acetate, and 25 ml of acetonitrile in a water bath, and the resultant product was stirred at room temperature for 4 hours, followed by leaving to stand overnight. 4.57 g of 1,8-diazabicyclo[5.4.0]-7-undecene (hereinafter, described to as DBU) was added dropwise to the mixture under ice-cooling. The mixture was stirred at room temperature for 1 hour. Thereafter, air was blown into the obtained mixture for 5 hours while stirring at room temperature. Ice and 1 M hydrochloric acid were added to the reaction mixture, and extraction thereof was performed using ethyl acetate. The organic layer was washed with saturated aqueous sodium bicarbonate solution and a saturated saline solution in this order, dried over anhydrous magnesium sulfate, and then concentrated under reduced pressure, thereby obtaining 2.83 g of 3-(2,6-difluorophenyl)-5-hydroxy-5-methyl-4-phenyl-2(5H)-furanone.

$^1$H-NMR (CDCl$_3$, TMS) δ (ppm): 1.78 (3H, s), 4.07 (1H, br s), 6.77-6.85 (1H, br m), 6.96-7.08 (1H, m), 7.29-7.38 (4H, m), 7.53-7.55 (2H, m)

0.60 g of hydrazine monohydrate was added dropwise to a mixture of 2.83 g of 3-(2,6-difluorophenyl)-5-hydroxy-5-methyl-4-phenyl-2(5H)-furanone and 15 ml of 1-butanol, followed by stirring at a bath temperature of 110° C. for 2.5 hours. Next, the reaction mixture was cooled to 0° C. The obtained solid was collected by filtration. The collected solid was washed with a mixed solvent (1:1) of hexane and t-butyl methyl ether, and dried under reduced pressure, thereby obtaining 1.70 g of 4-(2,6-difluorophenyl)-6-methyl-5-phenyl-2H-pyridazine-3-one. $^1$H-NMR (DMSO-d6, TMS) δ (ppm): 2.02 (3H, s), 6.92-6.98 (2H, m), 7.11-7.12 (2H, m), 7.27-7.36 (4H, m), 13.2 (1H, br s)

1.54 g of 4-(2,6-difluorophenyl)-6-methyl-5-phenyl-2H-pyridazine-3-one and 10 ml of phosphorus oxychloride were mixed, followed by stirring at a bath temperature of 110° C. for 1.5 hours. The reaction mixture was cooled to room temperature, and concentrated under reduced pressure. Ethyl acetate and ice water were added to the residue, and liquid-liquid separation was performed. The organic layer was washed with a saturated aqueous sodium bicarbonate solution and a saturated saline solution in this order, dried over anhydrous sodium sulfate, and then concentrated under reduced pressure. 1.55 g of the obtained residue was washed with a mixture of hexane and ethyl acetate (10:1), and then washed with tert-butyl methyl ether, thereby obtaining 0.85 g of the pyridazine compound (1). $^1$H-NMR (CDCl$_3$, TMS) δ (ppm): 2.55 (3H, s), 6.79-6.83 (2H, m), 7.07-7.09 (2H, m), 7.23-7.30 (4H, m)

Reference Preparation Example 2

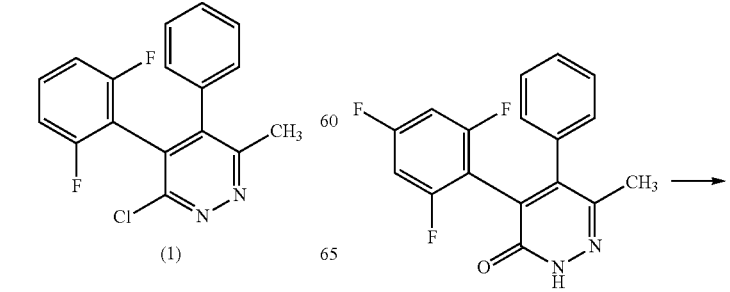

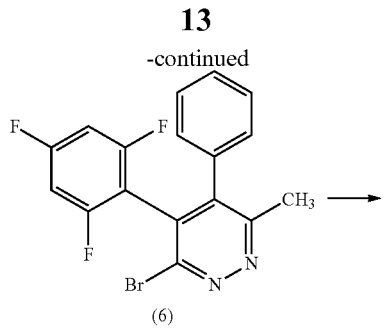

(6)

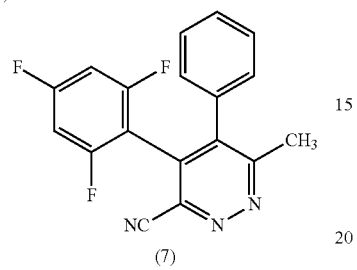

(7)

2.21 g of 6-methyl-5-phenyl-4-(2,4,6-trifluorophenyl)-2H-pyridazine-3-one and 8.0 g of phosphorous oxybromide were mixed, followed by stirring at 90° C. for 1.5 hours. The reaction mixture was cooled to room temperature, suspended in 20 ml of ethyl acetate, and 100 g of ice was added thereto. After neutralizing with sodium bicarbonate, extraction was performed on the residue using ethyl acetate, and liquid-liquid separation was performed. The organic layer was washed with saturated saline solution, dried over anhydrous magnesium sulfate, and then concentrated under reduced pressure. The obtained residue (2.42 g) was subjected to silica gel column chromatography, thereby obtaining 1.86 g of the pyridazine compound (6) as a white solid.

$^1$H-NMR (CDCl$_3$, TMS) δ (ppm): 2.52 (3H, s), 6.56-6.64 (2H, m), 7.05-7.07 (2H, m), 7.30-7.36 (3H, m)

1.26 g of the pyridazine compound (6), 0.44 g of copper cyanide, and 14 ml of N,N-dimethylacetamide were mixed, followed by stirring for 3 hours while heating to reflux. After the reaction mixture was cooled to room temperature, 100 ml of ethyl acetate and 100 ml of water were added thereto, and the resultant product was filtered using Celite (registered trademark). After liquid-liquid separating the filtrate, the organic layer was washed with saturated saline solution, dried over anhydrous magnesium sulfate, and then concentrated under reduced pressure. The obtained residue (1.07 g) was subjected to silica gel column chromatography, thereby obtaining 0.55 g of the pyridazine compound (7) as a light yellow solid.

$^1$H-NMR (CDCl$_3$, TMS) δ (ppm): 2.70 (3H, s), 6.63-6.69 (2H, m), 7.06-7.09 (2H, m), 7.34-7.40 (3H, m)

Reference Preparation Example 3

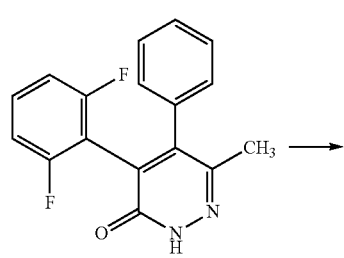

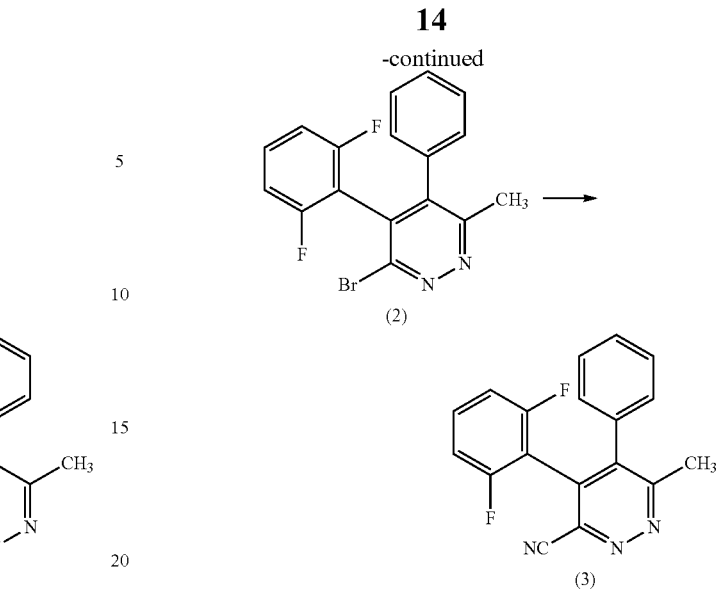

(2)

(3)

2.09 g of 4-(2,6-difluorophenyl)-6-methyl-5-phenyl-2H-pyridazine-3-one and 8.0 g of phosphorous oxybromide were mixed, followed by stirring at 90° C. for 1.5 hours. The reaction mixture was cooled to room temperature, suspended in 20 ml of ethyl acetate, and about 100 g of ice was added thereto. After neutralizing with sodium bicarbonate, extraction was performed on the residue using ethyl acetate, and liquid-liquid separation was performed. The organic layer was washed with water, dried over anhydrous magnesium sulfate, and then concentrated under reduced pressure. The obtained residue (2.00 g) was subjected to silica gel column chromatography, thereby obtaining 1.12 g of the pyridazine compound (2) as a solid.

$^1$H-NMR (CDCl$_3$, TMS) δ (ppm): 2.52 (3H, s), 6.78-6.84 (2H, m), 7.06-7.09 (2H, m), 7.22-7.30 (4H, m)

0.80 g of the pyridazine compound (2), 0.33 g of copper cyanide, and 10 ml of N,N-dimethylacetamide were mixed, followed by stirring for 3 hours while heating to reflux. After the reaction mixture was cooled to room temperature, 100 ml of ethyl acetate and 100 ml of water were added thereto, and the resultant product was filtered using Celite (registered trademark). After liquid-liquid separating the filtrate, the organic layer was washed with saturated saline solution, dried over anhydrous magnesium sulfate, and then concentrated under reduced pressure. The obtained residue (0.61 g) was subjected to silica gel column chromatography, thereby obtaining 0.40 g of the pyridazine compound (3) as a white solid.

$^1$H-NMR (CDCl$_3$, TMS) δ (ppm): 2.70 (3H, s), 6.86-6.90 (2H, m), 7.07-7.09 (2H, m), 7.30-7.38 (4H, m)

Reference Preparation Example 4

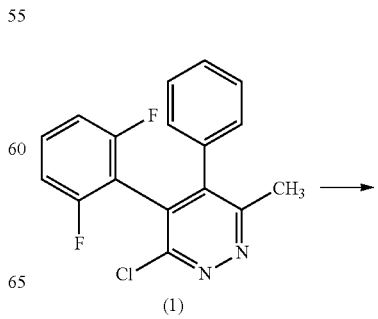

(1)

-continued

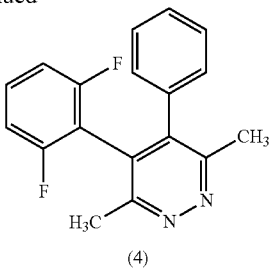

(4)

0.95 g of the pyridazine compound (1), 0.21 g of iron (III) acetylacetonate, 30 ml of tetrahydrofuran, and 3 ml of N-methylpyrrolidone were mixed, and 3 ml of methylmagnesium bromide (3.0 mol/L diethyl ether solution) was added thereto while stirring under ice-cooling. After stirring for 1 hour under ice-cooling, 15 ml of 0.33 mol/L aqueous hydrochloric acid solution was added dropwise to the reaction mixture, and thereafter water was added, extraction thereof was performed using ethyl acetate. The organic layer was washed with water, dried over anhydrous magnesium sulfate, and then concentrated under reduced pressure. The obtained residue (0.91 g) was subjected to silica gel column chromatography, thereby obtaining 0.82 g of the pyridazine compound (4) as a white crystal.

$^1$H-NMR (CDCl$_3$, TMS) δ (ppm): 2.51 (3H, s), 2.52 (3H, s), 6.74-6.82 (2H, m), 7.05-7.07 (2H, m), 7.18-7.30 (4H, m)

Reference Preparation Example 5

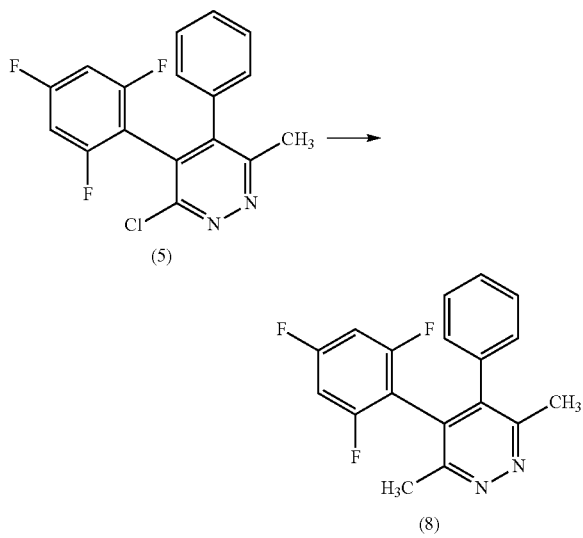

1.00 g of the pyridazine compound (5), 0.21 g of iron (III) acetylacetonate, 30 ml of tetrahydrofuran, and 3 ml of N-methylpyrrolidone were mixed, and 3 ml of methylmagnesium bromide (3.0 mol/L diethyl ether solution) was added thereto while stirring under ice-cooling. After stirring for 1 hour under ice-cooling, 15 ml of 0.33 mol/L aqueous hydrochloric acid solution was added dropwise to the reaction mixture, and thereafter water was added, extraction thereof was performed using ethyl acetate. The organic layer was washed with water, dried over anhydrous magnesium sulfate, and then concentrated under reduced pressure. The obtained residue (0.98 g) was subjected to silica gel column chromatography, thereby obtaining 0.82 g of the pyridazine compound (8) as a white crystal. $^1$H-NMR data substantially coincide with data described in WO2006/001175A1.

Formulation Example 1

2.5 parts of any one of the pyridazine compounds (1) to (8), 1.25 parts of fipronil, 14 parts of polyoxyethylene styrylphenyl ether, 6 parts of calcium dodecyl benzene sulfonate, and 76.25 parts of xylene are fully mixed, so as to obtain each formulation.

Formulation Example 2

2 parts of any one of the pyridazine compounds (1) to (8), 8 parts of fipronil, 35 parts of a mixture (weight ratio is 1:1) of white carbon and a polyoxyethylene alkyl ether sulfate ammonium salt, and 55 parts of water are mixed, and the mixture is subjected to fine grinding according to a wet grinding method, so as to obtain each formulation.

Formulation Example 3

5 parts of any one of the pyridazine compounds (1) to (8), 10 parts of fipronil, 1.5 parts of sorbitan trioleate and 28.5 parts of an aqueous solution containing 2 parts of polyvinyl alcohol are mixed, and the mixture is subjected to fine grinding according to a wet grinding method. Thereafter, 45 parts of an aqueous solution containing 0.05 parts of xanthan gum and 0.1 parts of aluminum magnesium silicate are added to the resultant mixture, and 10 parts of propylene glycol is further added thereto. The obtained mixture is blended by stirring, so as to obtain each formulation.

Formulation Example 4

1 part of any one of the pyridazine compounds (1) to (8), 4 parts of fipronil, 1 part of synthetic hydrated silicon oxide, 2 parts of calcium lignin sulfonate, 30 parts of bentonite, and 62 parts of kaolin clay are fully ground and mixed, and the resultant mixture is added with water and fully kneaded, and then subjected to granulation and drying, so as to obtain each formulation.

Formulation Example 5

12.5 parts of any one of the pyridazine compounds (1) to (8), 37.5 parts of fipronil, 3 parts of calcium lignin sulfonate, 2 parts of sodium lauryl sulfate, and 45 parts of synthetic hydrated silicon oxide are fully ground and mixed, so as to obtain each formulation.

Formulation Example 6

3 parts of any one of the pyridazine compounds (1) to (8), 2 parts of fipronil, 85 parts of kaolin clay, and 10 parts of talc are fully ground and mixed, so as to obtain each formulation.

Next, test examples are shown.

Test Example 1

A smearing treatment was performed on 10 g of wheat (cultivar; Shirogane) seeds naturally infected with a spore of pink snow rot (*Microdochium nivale*) with 100 μl of cyclohexanone solution containing the test compound of a predetermined weight using a rotary seed treatment machine (seed dresser, manufactured by Hans-Ulrich Hege GmbH).

One day after the above-described treatment, soil was packed in a plastic pot, and seeds treated with the test compound were seeded and cultivated for 20 days in a glass greenhouse (this was used as a treated area). Thereafter, the presence or absence of incidence of pink snow rot in seedlings budded from each seed was observed, and the incidence of disease was calculated by the following Formula (1).

On the other hand, wheat seeds on which the above-described smearing treatment was not performed were cultivated in the same manner as in the treated area (this was used as a non-treated area). Then, the incidence of disease was calculated in the same manner as in the treated area.

From each of the incidences of disease of the treated area and the non-treated area, the effect was calculated by the following Formula (2).

The results are shown in Tables 1 to 2.

Incidence of disease (5)=(Number of infected budded seedlings)/(Total number of budded seedlings)× 100   Formula (1)

Effect (%)=(1−Incidence of disease in treated area/ Incidence of disease in non-treated area)×100   Formula (2)

TABLE 1

| The pyridazine compound (1) [g/100 kg seeds] | Fipronil [g/100 kg seeds] | Effect (%) |
|---|---|---|
| 5 | 20 | 100 |

TABLE 2

| The pyridazine compound (3) [g/100 kg seeds] | Fipronil [g/100 kg seeds] | Effect (%) |
|---|---|---|
| 5 | 20 | 100 |

INDUSTRIAL APPLICABILITY

Plant diseases can be effectively controlled by using the composition for controlling plant diseases of the present invention.

The invention claimed is:

1. A composition for controlling plant diseases, containing a pyridazine compound represented by Formula (I) and fipronil, Formula (I)

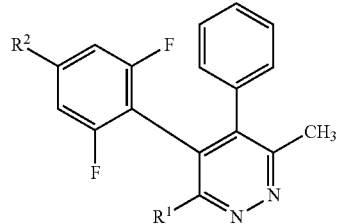

(I)

in the formula, $R^1$ represents a chlorine atom, a bromine atom, a cyano group, or a methyl group, and $R^2$ represents a hydrogen atom or a fluorine atom.

2. The composition for controlling plant diseases according to claim 1, wherein a weight ratio of the pyridazine compound to fipronil (the pyridazine compound/fipronil) is 1/1 to 1/100.

3. A method for controlling plant diseases, comprising a step of applying an effective amount of a pyridazine compound represented by Formula (I) and fipronil to a plant or soil for cultivating a plant, Formula (I)

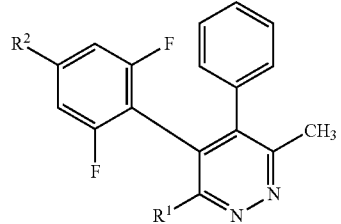

(I)

in the formula, $R^1$ represents a chlorine atom, a bromine atom, a cyano group, or a methyl group, and $R^2$ represents a hydrogen atom or a fluorine atom.

4. The method for controlling plant diseases according to claim 3, wherein a weight ratio of the pyridazine compound to fipronil (the pyridazine compound/fipronil) is 1/1 to 1/100.

5. The method for controlling plant diseases according to claim 3, wherein the plant or the soil for cultivating a plant is wheat or soil for cultivating wheat.

6. The method for controlling plant diseases according to claim 3, wherein the plant or the soil for cultivating a plant is plant seeds.

* * * * *